(12) United States Patent
Nan et al.

(10) Patent No.: US 9,612,180 B2
(45) Date of Patent: Apr. 4, 2017

(54) DYEING DEVICE AND METHOD OF USING A PADDLE DYEING MACHINE (71) Applicant: Shenzhen Mindray Bio-Medical Electronics Co., Ltd., Shenzhen (CN)

(72) Inventors: Yongtao Nan, Beijing (CN); William Li, Beijing (CN); Liangqing Chen, Beijing (CN); Lifang Dong, Beijing (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 301 days.

(21) Appl. No.: 14/512,226

(22) Filed: Oct. 10, 2014

(65) Prior Publication Data
US 2015/0030755 A1 Jan. 29, 2015

Related U.S. Application Data (63) Continuation of application No. PCT/CN2013/073892, filed on Apr. 8, 2013.

(30) Foreign Application Priority Data

Apr. 10, 2012 (CN) .......................... 2012 1 0103305

(51) Int. Cl.
*G01N 1/31* (2006.01)
*G01N 1/28* (2006.01)

(52) U.S. Cl.
CPC ........... *G01N 1/312* (2013.01); *G01N 1/2813* (2013.01); *G01N 1/31* (2013.01); *G01N 2001/315* (2013.01)

(58) Field of Classification Search
CPC .......................... G01N 1/31; G01N 2001/315
See application file for complete search history.

(56) References Cited

FOREIGN PATENT DOCUMENTS

| CN | 101957279 | 1/2011 |
|---|---|---|
| CN | 102053031 | 5/2011 |
| WO | WO2011/161353 | 12/2011 |

*Primary Examiner* — P. Kathryn Wright
(74) *Attorney, Agent, or Firm* — Kory D. Christensen; Stoel Rives LLP (57) ABSTRACT

A dyeing device of a smear machine may include a dyeing tank, a transmission mechanism and a work position set in an enclosed delivery channel of the transmission mechanism. The work position may include a blocking and separating mechanism, a reagent supplying and discharging mechanism, and a driving mechanism for driving the blocking and separating mechanism. The blocking and separating mechanism can operate for blocking a dyeing tank to be treated in a current work position, separating a treated dyeing tank and transmitting a separated dyeing tank to a next work position along the enclosed delivery channel. The reagent supplying and discharging mechanism can inject and/or discharge reagent into/from the dyeing tank. Various embodiments of this disclosure can transmit the dyeing tank within the enclosed transmission channel, block and separate the dyeing tank in the work position, and inject/discharge the dyeing solution into/from the dyeing tank as needed.

5 Claims, 8 Drawing Sheets

DYEING DEVICE AND METHOD OF USING A PADDLE DYEING MACHINE

TECHNICAL FIELD

This disclosure relates to medical equipment, and more particularly to dyeing devices and methods of using smear machines.

BACKGROUND

Traditional dyeing devices for automatic blood smears or other tissue smears commonly include two kinds of technologies: multi-slide dyeing technology and single-slide dyeing technology.

Multi-slide dyeing refers to putting multiple prepared smears into a device that may be similar to a basket. The device containing multiple smears is dyed in a dyeing tank. Smears are taken out after dyeing according to rules of procedure, while dyeing solution within the dyeing tank may be reused. Since the quality of the dyeing solution may be reduced after being reused repeatedly, the dyeing effect of different batches of dyeing smears cannot be guaranteed, and this may affect the diagnosis of related clinical pathology. Additionally, in practical usage, due to emergency treatment or other reasons, certain smears may need to be dyed quickly, so the dyeing solution used for multiple smears may only be used for one or a few smears. As a result, the availability of the dyeing solution may be reduced, causing waste, and the cost for dyeing one smear may be greatly increased.

Single-slide dyeing refers to dyeing prepared smears piece by piece in an individual dyeing tank. The dyeing tank is designed to be as small as possible, and it can only accommodate one smear, so as to reduce the amount of dyeing solution in the dyeing tank. Compared to multi-slide dyeing, fewer reagents may be needed for single-slide dyeing when there are a few smears to be dyed. When there are a lot of smears to be dyed, an equivalent amount of reagents may be consumed by using either multi-slide dyeing or single-slide dyeing. However, the quality of dyeing using the single-slide dyeing technology is apparently better than that using the multi-slide dyeing technology. Unfortunately, the dyeing tank of a traditional single-slide dyeing machine cannot be recycled, which may cause resource waste and low efficiency.

SUMMARY

This disclosure provides dyeing devices of smear machines that may achieve automatic recycling.

In one aspect, a dyeing device of a smear machine may include a dyeing tank, a transmission mechanism for recursively transmitting the dyeing tank in an enclosed delivery channel, and a work position arranged on the enclosed delivery channel. The work position may include a blocking and separating mechanism that can block a dyeing tank to be treated in a current work position and separate a treated dyeing tank so that a separated dyeing tank may be transferred to a next work position along the enclosed delivery channel by the transmission mechanism. The work position may also include a reagent supplying and discharging mechanism that can inject and/or discharge reagent to/from the dyeing tank, and a driving mechanism that can drive the blocking and separating mechanism.

In some embodiments, the transmission mechanism may include a round tray driven by a motor, and the round tray may be supplied with an annular opening used to suspend the dyeing tank.

In some embodiments, the dyeing tank may include a body that may be equipped with an opening cavity for accommodating reagent(s) and smear(s). Both sides of the body may be equipped with a suspension end for suspending the dyeing tank on the transmission mechanism, and the suspension end may be equipped with a slot for separation by the blocking and separating mechanism.

In some embodiments, the blocking and separating mechanism may include a claw arm that may be linked with the driving mechanism and may be driven to move by the driving mechanism. The claw arm may include a blocking part, a separating part, and a linking part that can fixedly connect the blocking part with the separating part. The blocking part and the separating part may be driven by the driving mechanism to be alternately located in the enclosed delivery channel of the dyeing tank, and the blocking part and the separating part may be set front and back in the channel along a direction of transmitting the dyeing tank by the transmission mechanism.

In some embodiments, the number of claw arms may be about two. Whereas the blocking part and the separating part of the same claw arm may be set on both sides of a target dyeing tank, the blocking parts of the two claw arms may both be set in a front orientation along the direction of transmitting the target dyeing tank, and the separating parts of the two claw arms may both be set in a rear orientation along the direction of transmitting the target dyeing tank.

In some embodiments, each work position can also include a detection device that can detect a position of the dyeing tank, and the detection device may be connected with the driving mechanism. The dyeing tank can also include a position detection plate for detection.

In another aspect, a dyeing method of a smear machine may include:

driving a transmission mechanism to move to transmit a dyeing tank circularly in an enclosed delivery channel;

blocking a dyeing tank to be treated in a current work position;

treating the dyeing tank blocked in the current work position; and separating a treated dyeing tank and transmitting it to a next work position along the enclosed delivery channel.

In some embodiments, the treatment may include at least one of: blocking the dyeing tank for a preset time, injecting reagent into the dyeing tank or discharging reagent from the dyeing tank.

In some embodiments, the enclosed delivery channel may be a circular channel.

In some embodiments, blocking the dyeing tank to be treated in the current work position may include: driving a blocking part of a claw arm so as to set the blocking part within the enclosed delivery channel of the dyeing tank in a front orientation; and separating the treated dyeing tank may include: driving the blocking part of the claw arm to deviate from the enclosed delivery channel of the dyeing tank, while driving a separating part of the claw arm to be arranged within the enclosed delivery channel of the dyeing tank, where the blocking part and the separating part may be set front and back in the channel along a direction of transmitting the dyeing tank by the transmission mechanism.

In some embodiments, the dyeing method may further include injecting dyeing solutions into the dyeing tank, and then putting a smear that needs to be dyed into the dyeing tank.

The dyeing devices and methods of the smear machines described above can transmit the dyeing tank within the enclosed delivery channel, block and separate the dyeing tank in the work position, and inject/discharge the dyeing solutions or cleaning solutions into/from the dyeing tank as needed, in which case every dyeing tank may be reused circularly so as to improve working efficiency.

BRIEF DESCRIPTION OF THE DRAWINGS

FIG. 7 is a working schematic of a blocking and separating mechanism in.

DETAILED DESCRIPTION

Figure 1:
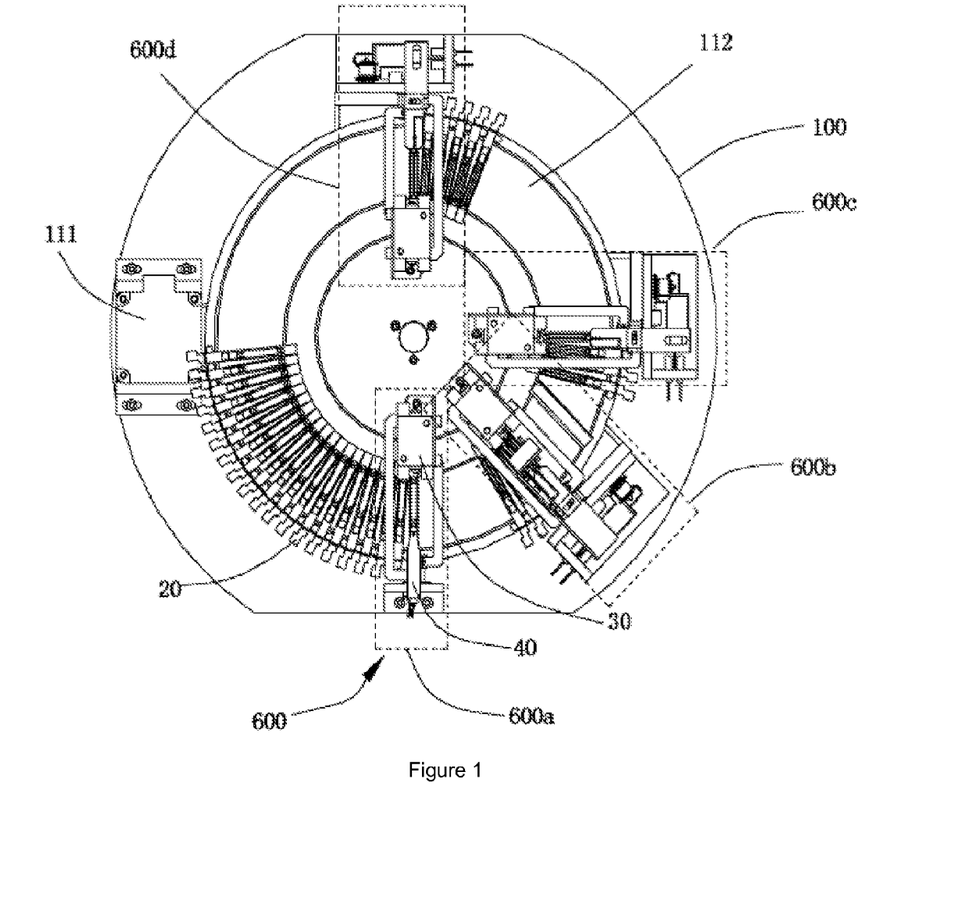
FIG. 1 is an overlooking structural schematic of a dyeing device of a smear machine according to an embodiment of this disclosure.
Figure 2:
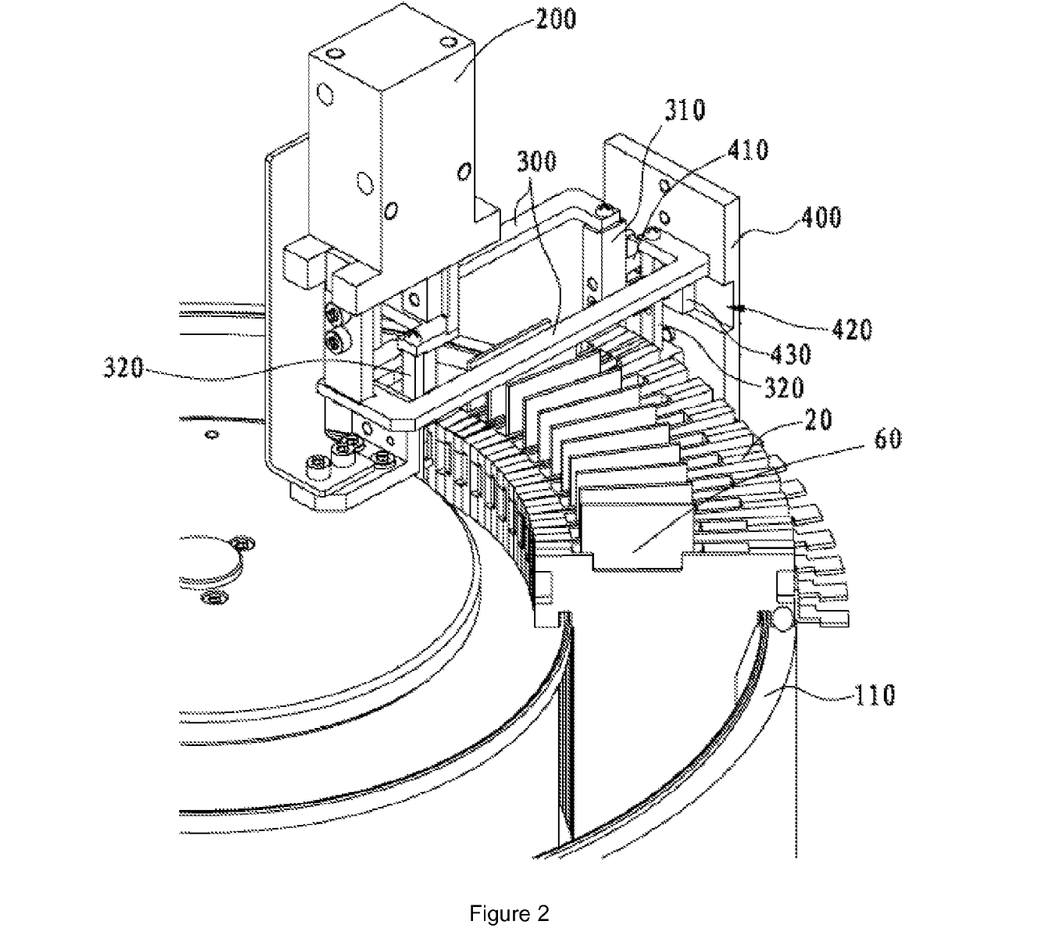
FIG. 2 is a structural schematic of a blocking and separating mechanism.

FIGS. 1 and 2 illustrate a dyeing device of a smear machine. The dyeing device of the smear machine may include several dyeing tanks 20, a transmission mechanism 100 and work positions 600. A number of dyeing tanks 20 may be suspended on the transmission mechanism 100, and the transmission mechanism 100 can transmit the dyeing tank(s) 20 for single-slide dyeing circularly in an enclosed delivery channel. The work positions 600 may be set in the enclosed delivery channel, and the work positions 600 may include a blocking and separating mechanism 30, a reagent supplying and discharging mechanism 40 and a driving mechanism 200. The blocking and separating mechanism 30 may be used for blocking a dyeing tank 20 to be treated in a current work position and separating a treated dyeing tank 20 so as to transmit a separated dyeing tank 20 to a next work position along the enclosed delivery channel by the transmission mechanism 100. The reagent supplying and discharging mechanism 40 can inject and/or discharge reagent to/from the dyeing tank 20 as needed. The driving mechanism 200 can drive the blocking and separating mechanism 30. The dyeing tank 20 may be kept to be transmitted in the enclosed delivery channel circularly by the dyeing device of the smear machine. The work position (s) 600 can block and separate the dyeing tank 20 as needed, and reagent may be injected/discharged into/from the dyeing tank 20 as needed. In this way, the dyeing tank 20 may be reused circularly and working efficiency may be improved.

As illustrated, at the same time, because the dyeing device of the smear machine is independent of other mechanisms of the dyeing machine, the dyeing tank 20 may no longer take part in delivery and/or loading in the work procedure of other mechanisms of the dyeing machine. Dyeing solution may be injected into the dyeing tank 20 in the beginning of a dyeing process, and then a smear 60 that needs to be dyed may be put into the dyeing tank 20 so as to avoid risk of hemolysis and ensure quality of dyeing.

As illustrated, the dyeing tank 20 may be suspended on the transmission mechanism 100, and thus the dyeing tank 20 may be driven by the transmission mechanism 100 because of contact friction between the transmission mechanism 100 and the dyeing tank 20. The dyeing tank 20 can circularly rotate together with the transmission mechanism 100. When external force is applied to the dyeing tank 20 and is stronger than the contact friction between the dyeing tank 20 and the transmission mechanism 100, the dyeing tank 20 may be blocked at the position where the external force is applied; that is, the dyeing tank 20 can slide relative to the transmission mechanism 100. When the external force disappears, the dyeing tank 20 may again be transmitted sequentially by the transmission mechanism 100. The blocking and separating mechanism 30 of each work position in the dyeing device of the smear machine may be based on such a theory to realize the blocking and separation of the dyeing tank. When the dyeing tank is blocked by the work position, the smear 60 that needs to be dyed may be placed in the blocked dyeing tank 20 until the blocking and separating mechanism 30 releases the blocked dyeing tank 20. The released dyeing tank 20 can rotate with the transmission mechanism 100 and can enter the next work position.

Figure 8:
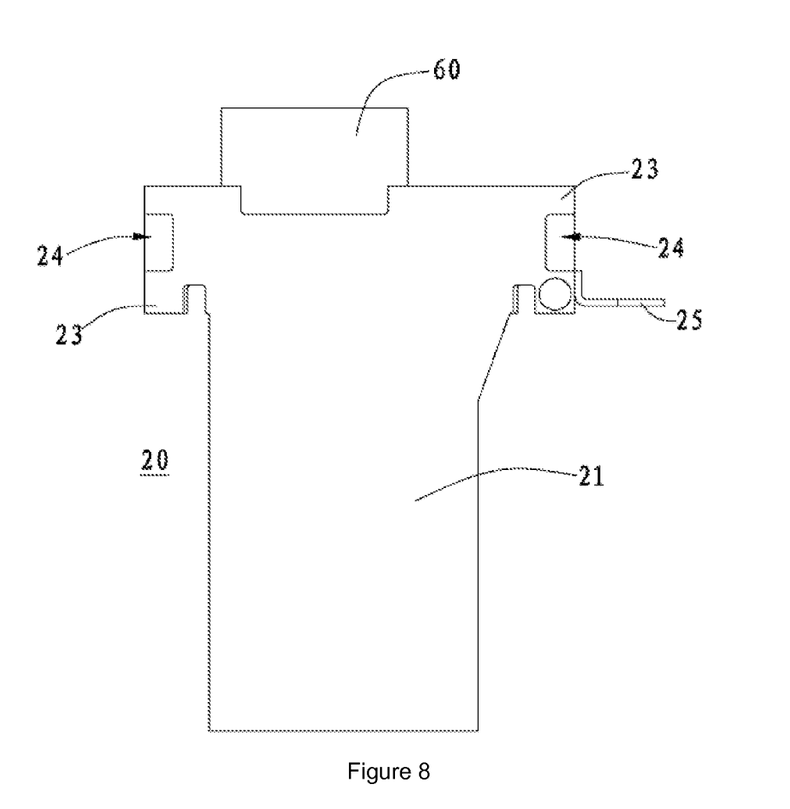
FIG. 8 is a front-side structural schematic of a single-slide dyeing tank.
Figure 9:
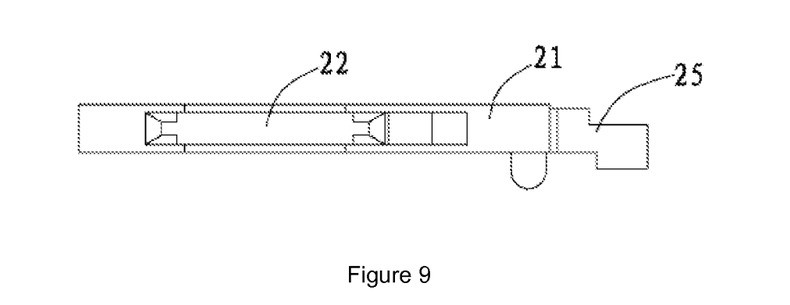
FIG. 9 is an overlooking structural schematic of a single-slide dyeing tank.

As shown in FIGS. 8 and 9, in order to cooperate with the blocking and separating mechanism 30, in some embodiments, the single-slide dyeing tank 20 may include a body 21. The body 21 may be equipped with an opening cavity 22 for accommodating reagent and the smear 60, and both sides of the body 21 may be equipped with a suspension end 23 for suspending the dyeing tank 20 on the transmission mechanism 100. The suspension end 23 may be equipped with a slot 24 for separation by the blocking and separating mechanism 30. Of course, in order to suspend the dyeing tank 20 on the transmission mechanism 100 more stably, in some embodiments, the suspension end 23 may be set in an upper portion of the two sides of the body 21.

As FIGS. 1 and 2 illustrate, in some embodiments, the transmission mechanism 100 may include a motor 111 and a round tray 110 driven by the motor 111. The motor 111 can drive the round tray 110 counterclockwise, and the round tray 110 may be equipped with a circle of enclosed delivery channel formed by an annular opening 112 for suspending the single-slide dyeing tank. Alternatively, the round tray 110 can also rotate clockwise. Additionally, the enclosed delivery channel of the transmission mechanism 100 can be in other formats or other shapes if only the transmission mechanism can transmit the dyeing tank 20 circularly, such as a runway of a stadium with two parallel straight lines connected by two semicircles.

Figure 3:
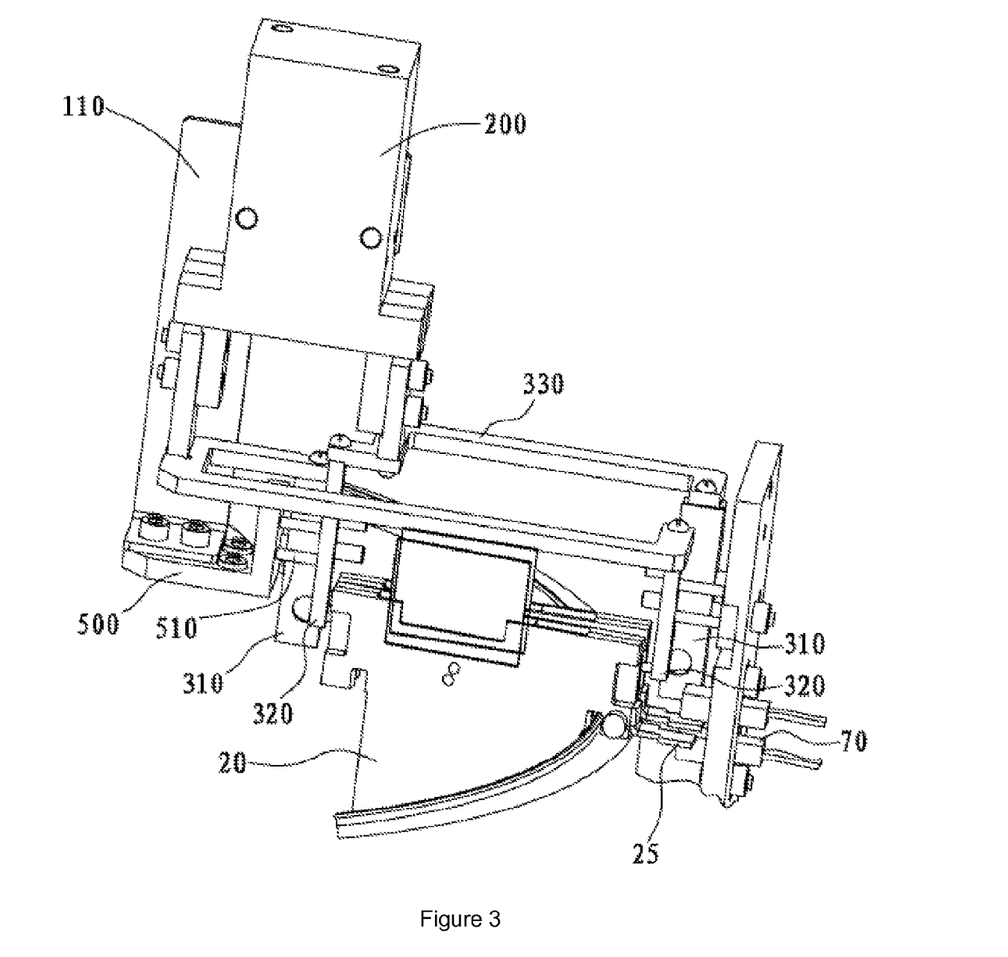
FIG. 3 is another structural schematic view of the blocking and separating mechanism shown in FIG. 2.

As FIGS. 2 and 3 illustrate, in some embodiments, the blocking and separating mechanism 30 may include a claw arm 300 connected to the driving mechanism 200, and the claw arm 300 may be driven to move by the driving mechanism 200. The claw arm 300 may include a blocking part 310, a separating part 320, and a linking part 330 that can fixedly connect the blocking part 310 and the separating part 320. The blocking part 310 and the separating part 320 may be driven by the driving mechanism 200 to be alternately located in the enclosed delivery channel of the dyeing tank 20, where the blocking part 310 and the separating part 320 may be set front and back in the channel along a direction of transmitting the dyeing tank 20 by the transmission mechanism 100.

As illustrated, the blocking part 310 and the separating part 320 may be driven by the driving mechanism 200 to be alternately located in the enclosed delivery channel of the transmission mechanism 100 for transmitting the dyeing tank 20, and the blocking part 310 and the separating part 320 may be set front and back in the channel along the direction of transmitting the dyeing tank 20 by the transmission mechanism 100. Based on the above-described arrangement, the blocking part 310 can first block the dyeing tank 20 in the channel for a preset time, the blocking part 310 can then move out of the channel and the separating part 320 can move into the channel. Because of the interval between the blocking part 310 and the separating part 320, the separating part 320 may be inserted along a rear orientation of a forefront dyeing tank 20 to block the dyeing tanks behind the forefront dyeing tank 20. The blocking part 310 and the separating part 320 may be fixedly connected as a whole by the linking part 330, so that a fixed interval may be achieved, and cooperation error may be avoided between the blocking part 310 and the separating part 320.

In some embodiments, the number of claw arms may be about two, and the blocking part 310 and the separating part 320 of the same claw arm may be set on both sides of the target dyeing tank 20. The blocking parts 310 of the two claw arms 300 can both be set in a front orientation along the direction of transmitting the target dyeing tank, and the separating parts 320 of the two claw arms 300 may be set in a rear orientation along the direction of transmitting the target dyeing tank. Two claw arms can block and separate the dyeing tank more stably. In other embodiments, however, there may be only one claw arm. In addition, when needed to block and separate the dyeing tank at numerous locations, approximately three, four or more claw arms may be used.

Figure 4:
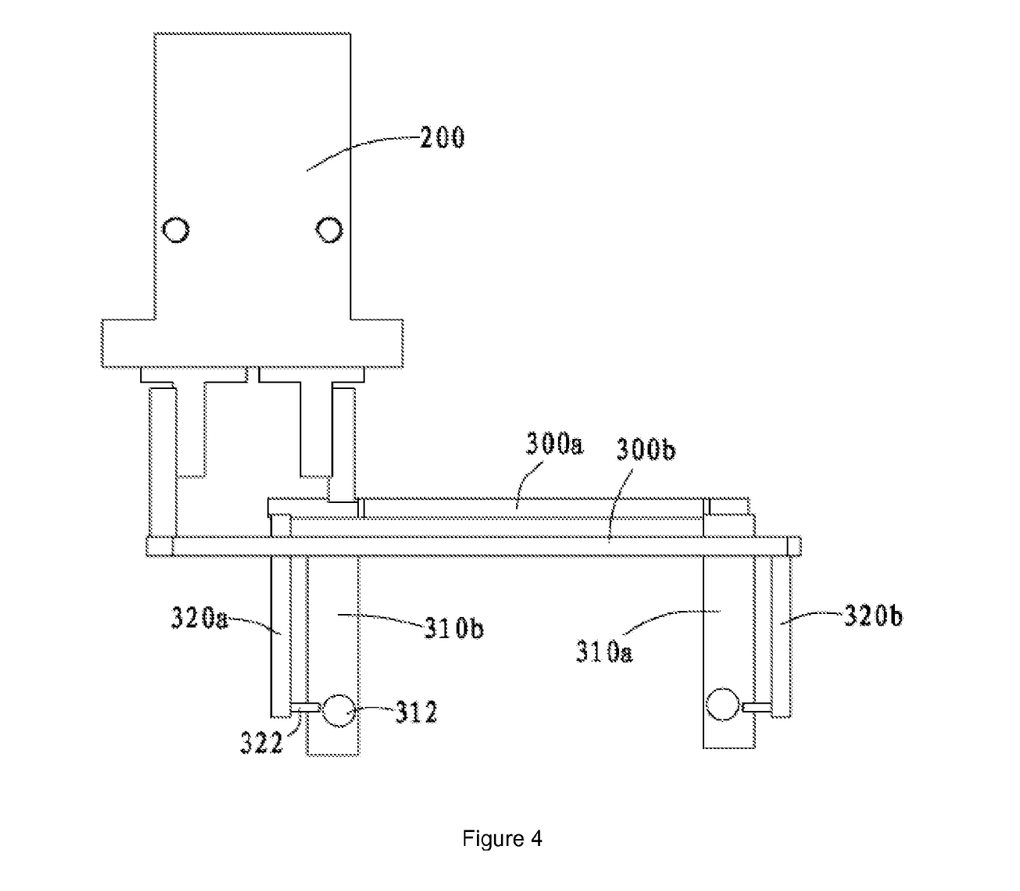
FIG. 4 is a front-side structural schematic of a blocking and separating mechanism wherein a blocking part is blocking a dyeing smear, while a separating part is separated from being in contact with the dyeing smear.

When two claw arms are used to achieve such blocking and separation at one location, the claw arm 300 may include a first claw arm 300a and a second claw arm 300b as shown in FIGS. 2-4. The first claw arm 300a and the second claw arm 300b can make reciprocating movements along a straight line. The movement direction of the first claw arm 300a and the second claw arm 300b may be perpendicular to the direction of transmitting the target dyeing tank. Specifically, the first claw arm 300a and the second claw arm 300b can make reciprocating movements along a radial direction of the transmission mechanism.

As illustrated, the first claw arm 300a may include a first blocking part 310a and a first separating part 320a. The second claw arm 300b may include a second blocking part 310b and a second separating part 320b. The first blocking part 310a and the first separating part 320a may be set on both sides of the target dyeing tank 20. The second blocking part 310b and the second separating part 320b may be set on both sides of the target dyeing tank 20. The first blocking part 310a and the second blocking part 310b can both be arranged in a front orientation along the direction of transmitting the target dyeing tank 20. The first separating part 320a and the second separating part 320b may both be set in a rear orientation along the direction of transmitting the target dyeing tank 20.

Figure 5:
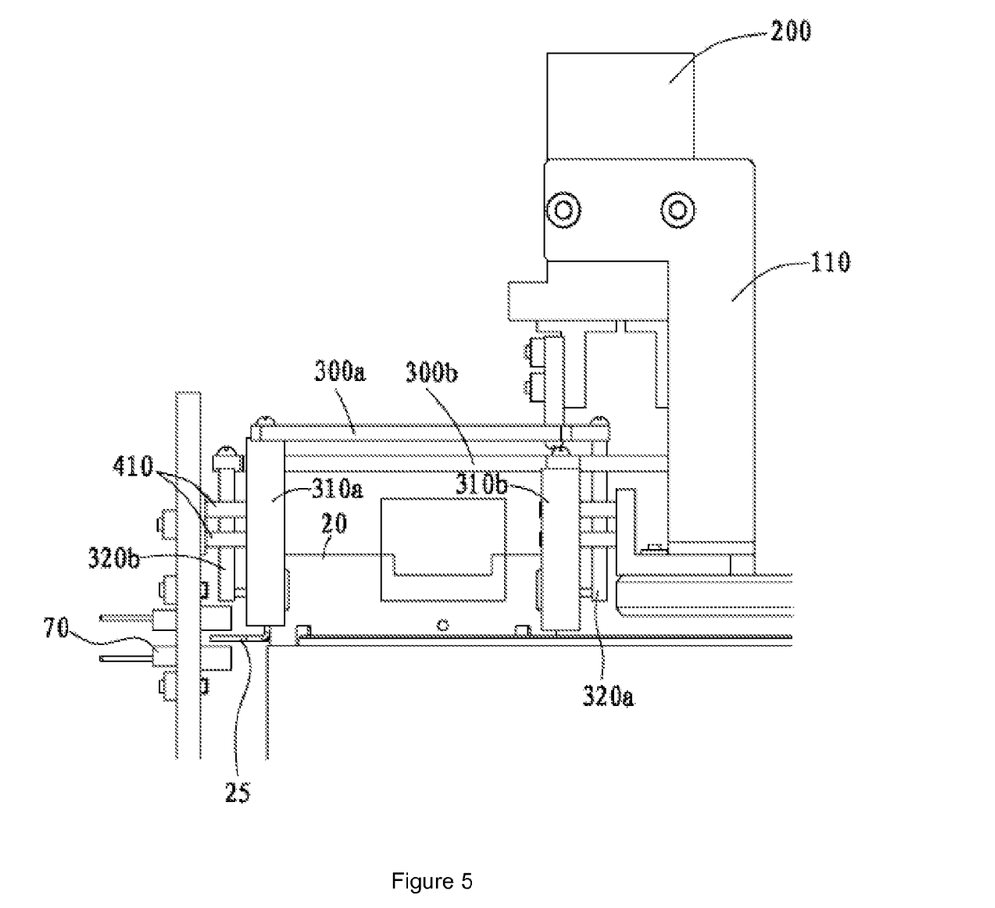
FIG. 5 is a working schematic of a blocking and separating mechanism.

FIGS. 2 to 5 illustrate multiple dyeing tanks 20 being transmitted by the transmission mechanism 100 during operation. In an initial state, the first blocking part 310a and the second blocking part 310b may both be arranged inside the channel of the transmission mechanism 100 for transmitting the dyeing tank, while the first separating part 320a and the second separating part 320b may be arranged outside of the channel of the transmission mechanism 100 for transmitting the dyeing tank (as shown in FIGS. 4 and 5). When the first dyeing tank 20 is transmitted to the position of the blocking part 310 by the transmission mechanism 100, the first blocking part 310a and the second blocking part 310b can press close to the dyeing tank 20 from both sides and block the front orientation along the direction of transmitting the dyeing tank so as to stop the dyeing tank 20.

Figure 6:
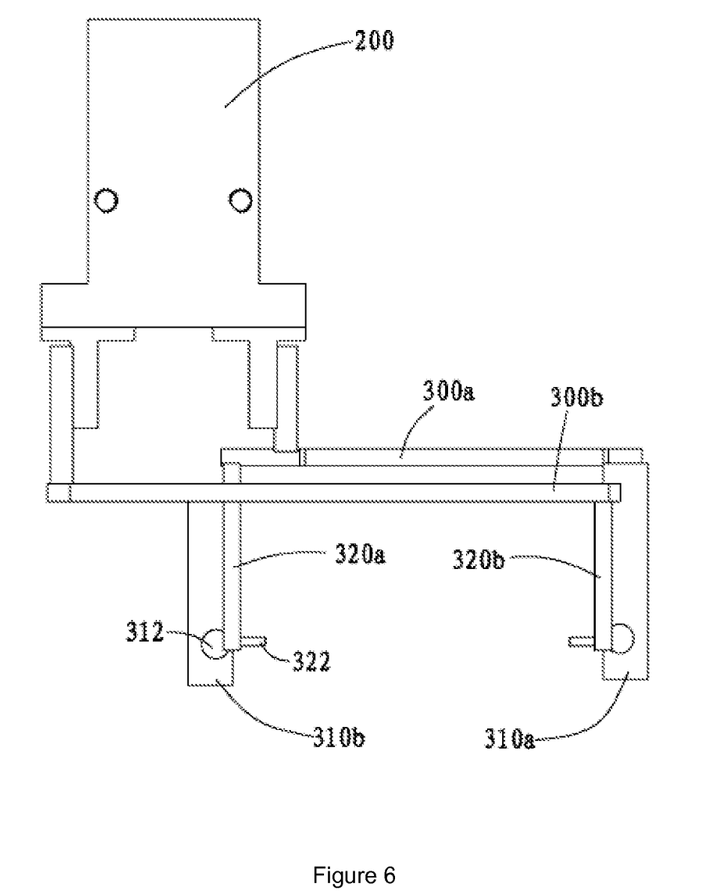
FIG. 6 is a front-side structural schematic of a blocking and separating mechanism wherein a separating part is in contact with a dyeing smear, while a blocking part is deviated from the dyeing smear.
Figure 7:
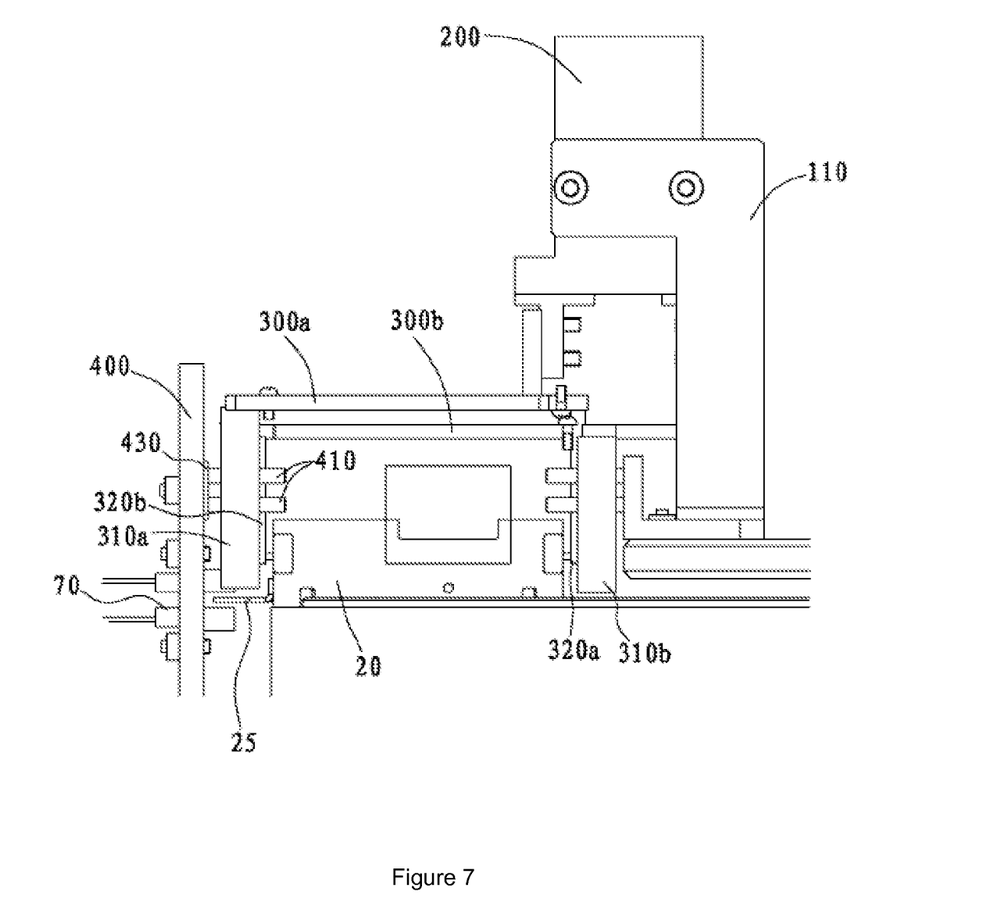

As FIGS. 6 and 7 illustrate, after the smear is dyed by the first dyeing tank, the driving mechanism 200 can drive the first claw arm 300a to move to an outer side of the transmission mechanism 100 and drive the second claw arm 300b to move to an inner side of the transmission mechanism 100. The first blocking part 310a and the second blocking part 310b may be far away from the dyeing tank 20, and the first dyeing tank 20 may be driven to move away by the transmission mechanism 100 when the resistance on the first dyeing tank 20 disappears. At the same time, the first separating part 320a and the second separating part 320b can enter into the channel of the transmission mechanism 100 for transmitting the dyeing tank 20. The first separating part 320a and the second separating part 320b can get stuck between the first dyeing tank and a second dyeing tank, and the second dyeing tank may be blocked from moving so as to separate the first dyeing tank from the second dyeing tank.

As illustrated, the driving mechanism 200 can drive the first claw arm 300a to move to the inner side of the transmission mechanism 100, and drive the second claw arm 300b to move to the outer side of the transmission mechanism 100 after the separation. The first blocking part 310a and the second blocking part 310b can move back to the channel of the transmission mechanism 100 for transmitting the dyeing tank 20, while the first separating part 320a and the second separating part 320b may move out of the channel of the transmission mechanism 100 for transmitting the dyeing tank 20 (as shown in FIGS. 4 and 5). The second dyeing tank may be released by the first separating part 320a and the second separating part 320b and may be driven to move by the transmission mechanism 100. However, when the second dyeing tank is driven to the position of the first blocking part 310a and second blocking part 310b, the first blocking part 310a and the second blocking part 310b can block the front orientation along the direction of transmitting the second dyeing tank 20 so as to stop the second dyeing tank and keep this state to finish the dyeing. Such blocking and separation may be performed cyclically to achieve continuous operation.

As illustrated, in some embodiments, linear reciprocating movements by the first claw arm 300a and the second claw arm 300b can realize the blocking and separating movements of the blocking and separating mechanism. The opening and closing action of the linear reciprocating movement may be simpler and quicker for driving the blocking part 310 and the separating part 320 to block the dyeing tank 20 alternately. However, the implementation is not limited to the opening and closing action of the linear reciprocating movement. In another embodiment, the first claw arm and the second claw arm can rotate around a hinged element to realize the blocking and the separation. In any other embodiments, the first claw arm and the second claw arm can move in other ways to realize the purpose of blocking the dyeing tank alternately by the blocking part and the separating part driven by the claw arm.

As illustrated, it will be understood that the first claw arm 300a and the second claw arm 300b may be set in this embodiment. In this case, the blocking operation may be synchronously achieved from the two sides of the dyeing tank 20 by the first blocking part 310a and the second blocking part 310b, and the blocking operation can also be synchronously achieved from both sides of the dyeing tank 20 by the first separating part 320a and the second separating part 320b, so that the resistance opposite to the transmitting direction may be evenly applied to both sides of the dyeing tank 20 to avoid any position offset of the dyeing tank 20 relative to the transmission mechanism 100. In any other embodiment, if the working condition can disregard the impact of position offset of the blocking part and the separating part on the dyeing tank, the claw arm may be set by other methods. For example, a single claw arm may be set, and the claw arm may be provided with a blocking part and a separating part, where the blocking part and the separating part may be respectively arranged on both sides of the dyeing tank, and the width of the separating part and the blocking part may be increased appropriately to keep stability. In this case, the blocking and the separating operations can also be realized alternately when the claw arm moves.

As FIGS. 4 and 6 illustrate, in some embodiments, a side of the blocking part 310 facing the direction of transmitting the dyeing tank may be equipped with an absorbing part 312, and the absorbing part 312 may be equipped with magnetic materials. When blocking, the blocking part 310 can absorb the dyeing tank 20 by the absorbing part 312 and an iron part or a magnetic part in the dyeing tank 20. In this way, the dyeing tank 20 may be blocked more steadily by the blocking part 310.

As FIGS. 4 and 6 illustrate, in some embodiments, the separating part 320 can stretch out to form a separating pin 322 that may be inserted between two adjacent dyeing tanks. The separating part 320 may be inserted between two adjacent dyeing tanks 20 to implement the separating operation by the separating pin 322. In some preferred embodiments, the separating pin 322 may be set on the separating part 320 detachably. If any state such as abrasion happens to the separating pin 322 because of the repeating movement, the separating pin 322 may be dismantled and replaced so as to improve work reliability and prolong work lifetime.

As FIGS. 3, 5 and 7 illustrate, in some embodiments, each work position 600 can also include a detection device 70 for detecting a position of the dyeing tank, where the detection device 70 may be connected with the driving mechanism 200 that drives the claw arm 300. Based on the detection device 70, the dyeing device can accurately control the blocking and separating actions and the injecting and discharging actions of the reagent supplying and discharging mechanism 40.

In some embodiments, the detection device 70 may be a detection device 70 having a detection optocoupler, and the detection device 70 may be set on a lateral fixed frame 400 of the blocking and separating mechanism 30. Alternatively, the detection device 70 may be of another type that can realize the purpose of sampling a position signal of the dyeing tank 20 and outputting the signal to the driving mechanism 200. There may be alternative solutions in the field of position detection technology, which do not need to be described in detail here.

As FIGS. 8 and 9 illustrate, in some embodiments, in order to match up with the detection of the detection device 70, the single dyeing tank may be equipped with a position detection plate 25 for detection. As FIGS. 5 and 7 illustrate, if the detection device 70 has a detection optocoupler, the dyeing tank 20 may be transmitted to the position of the detection device 70 by the transmission mechanism 100, and the position detection plate 25 may be inserted into the detection optocoupler, so that the detection optocoupler can sample signal(s) and transmit the signal(s) to the driving mechanism 200, in which case the driving mechanism 200 can control the action of the claw arm 300.

In some embodiments, the detection device 70 can have a detection optocoupler for detection, and the detection device 70 may be set on a lateral fixed frame 400 of the dyeing device of the smear machine. In other embodiments, the detection device 70 may be another type of detection device that can realize the purpose of sampling a position signal of the dyeing tank 20 and outputting the signal to the driving control mechanism. There may be alternative solutions in the field of position detection technology, which do not need to be described in detail here.

As FIGS. 2 and 3 illustrate, in some embodiments, a guiding mechanism may be movably inserted into an end of the claw arm 300. To be specific, the guiding mechanism may include a first guiding pillar 410 installed on the lateral fixed frame 400, and a second guiding pillar 510 installed on a central fixed frame 500 of the dyeing device of the smear machine. Alternatively, there may be one or more than two guiding pillars. The end of the claw arm 300 may be equipped with a guiding hole for cooperating with the guiding mechanism at a position corresponding to the first guiding pillar 410 and the second guiding pillar 510, and the end of the claw arm 300 can slide along the first guiding pillar 410 and the second guiding pillar 510 through the guiding hole. An axial direction of the first guiding pillar 410 and the second guiding pillar 510 may be the same as a moving direction of the end of the claw arm 300. In this way, structural strength of the claw arm 300 may be improved without affecting the movement of the claw arm 300 for realizing the separating and the blocking actions. The end of the claw arm 300 may be one, all or a combination of the first blocking part 310a, the second blocking part 310b, the first separating part 320a and the second separating part 320b.

As FIG. 2 illustrates, in some embodiments, the blocking and separating device of the dyeing tank of the smear machine may also include a position regulating mechanism, and the guiding mechanism may be set on the position regulating mechanism. To be specific, the position regulating mechanism may include a guiding block 430 that may be set in a guiding slot 420 of the lateral fixed frame 400. The guiding block 430 may be slidably set in the guiding slot 420, and the first guiding pillar 410 of the guiding mechanism may be set fixedly on the guiding block 430. When the installation position of the claw arm 300 needs to be adjusted, the guiding block 430 can slide along the guiding slot 420, and the claw arm 300 may be adjusted to a proper position by the guiding mechanism. After the position adjustment is completed, the position of the guiding block 430 may be restricted in the guiding slot 420; that is, the guiding mechanism may be fixed. In some embodiments, the suspension end of the dyeing tank may be equipped with the slot 24. When the blocking and separating mechanism 30 works, the separating part 320 may be smoothly inserted between two adjacent dyeing tanks 20 so as to prevent the separating part 320 from directly striking the body 21 of the dyeing tank 20, to improve work reliability.

As shown in FIG. 1, approximately four work positions may be arranged in this embodiment. The blocking and separating mechanism 30 of a first work position 600a can block empty dyeing tanks 20 in front of it; the reagent supplying and discharging mechanism 40 can inject reagent as needed (called reagent A below) into the empty dyeing tank 20 at the first work position 600a; and then the smear 60 that needs to be dyed may be put into this empty dyeing tank 20. When necessary, the blocking and separating mechanism 30 can separate the dyeing tank 20 equipped with the smear 60 from other dyeing tanks without the smear, and the dyeing tank 20 equipped with the smear 60 can go through the first work position 600a and rotate with the transmission mechanism 100 until it is blocked by the blocking and separating mechanism 30 of a next work position.

When the dyeing tank 20 equipped with the smear 60 arrives at a second work position 600b, the blocking and separating mechanism 30 can fix the dyeing tank 20 equipped with the smear 60 on the corresponding position of the reagent supplying and discharging mechanism 40, and the dyeing tank 20 may be detected and confirmed by the detection device 70 arranged at this position. According to the dyeing procedure, after the smear 60 is steeped in the dyeing tank 20 with reagent A for a preset time, the reagent supplying and discharging mechanism 40 may be inserted into the dyeing tank 20, discharge the reagent A from the dyeing tank, and inject another reagent (called reagent B below) into the dyeing tank 20. After that, the blocking and separating mechanism 30 can block subsequent dyeing tanks at the second position 600b and let the dyeing tank 20 injected with reagent B pass, after which the dyeing tank 20 can arrive at a next blocking position with the rotation of the transmission mechanism 100.

When the dyeing tank 20 equipped with the smear 60 arrives at a third work position 600c, the blocking and separating mechanism 30 can fix the dyeing tank 20 equipped with the smear 60 on the corresponding position of the reagent supplying and discharging mechanism 40, and the dyeing tank 20 may be detected and confirmed by the detection device 70 arranged at this position. According to the dyeing procedure, after the smear 60 is steeped in the dyeing tank 20 with reagent B for a preset time, the reagent supplying and discharging mechanism 40 can be inserted into the dyeing tank 20, discharge the reagent B from the dyeing tank, and inject another reagent (called reagent C below) into the dyeing tank 20. After that, the blocking and separating mechanism 30 can block subsequent dyeing tanks at the third position 600c and can let the dyeing tank 20 injected with reagent C pass, after which the dyeing tank 20 can arrive at a next blocking position with the rotation of the transmission mechanism 100.

When the dyeing tank 20 equipped with the smear 60 arrives at a fourth work position 600d, the blocking and separating mechanism 30 can fix the dyeing tank 20 equipped with the smear 60 on the corresponding position of the reagent supplying and discharging mechanism 40, and the dyeing tank 20 may be detected and confirmed by the detection device 70 arranged at this position. According to the dyeing procedure, after the smear 60 is steeped in the dyeing tank 20 with reagent C for a preset time, the reagent supplying and discharging mechanism 40 can be inserted into the dyeing tank 20, discharge the reagent C in the dyeing tank, and inject clean water into the dyeing tank to clean the smear 60. The smear 60 may be taken away for subsequent processes after cleaning. After that, the blocking and separating mechanism 30 can block subsequent dyeing tanks at the fourth work position 600d and let the empty dyeing tank 20 go, after which the dyeing tank 20 can rotate with the transmission mechanism 100 to an area that stores the dyeing tank(s) for the next recycle process.

As illustrated, each work position in this embodiment can work individually so that multiple smears may be dyed at the same time.

Various embodiments of this disclosure are not limited to four work positions; there may be about two, three or five work positions, etc. When many work positions exist, a relative angle between the work positions can also be optimized according to the dyeing process frequently used by users. In some extreme conditions, there may be only one work position: the dyeing tank can return through the enclosed delivery channel to the same work position for further treatment, and the smear may be inserted or taken out by an operator or by a machine in other positions. The treatment described above may be at least one of following: blocking the dyeing tank for a preset time, injecting the reagent into the dyeing tank or discharging the reagent from the dyeing tank. That is to say, the dyeing tank may be blocked for a preset time without the reagent being injected or discharged, or the reagent may be injected into or discharged from the dyeing tank without blocking the dyeing tank, or the reagent may be injected into and discharged from the dyeing tank while the dyeing tank has been blocked for a preset time.

In the above-described dyeing devices of the smear machine as an independent product, the dyeing tank may be one part of the dyeing device of the smear machine, and the dyeing tank can also be an external component involved in the working procedure of the dyeing device of the smear machine.

In addition, a dyeing method of using a smear machine can also be provided, which may include the following: driving a transmission mechanism to move so as to transmit a dyeing tank circularly in an enclosed delivery channel; blocking a dyeing tank to be treated in a current work position; treating the dyeing tank blocked in this work position; and separating a treated dyeing tank so as to transmit the treated dyeing tank to a next work position along the enclosed delivery channel.

In some embodiments, the treatment may be at least one of the following: blocking the dyeing tank for a preset time, and injecting reagent into the dyeing tank or discharging reagent from the dyeing tank. That is to say, the dyeing tank may be blocked for a preset time without the reagent being injected or discharged, or the reagent may be injected into or discharged from the dyeing tank without blocking the dyeing tank, or the reagent may be injected into and discharged from the dyeing tank while the dyeing tank has been blocked for a preset time.

In some embodiments, the enclosed delivery channel of the above-described dyeing method of using a smear machine may be a round channel.

In some embodiments of the dyeing method of using a smear machine, blocking the dyeing tank to be treated in the current work position may include driving a blocking part of a claw arm so as to set the blocking part within the enclosed delivery channel of the dyeing tank in a front orientation; and separating the treated dyeing tank may include driving the blocking part of the claw arm to deviate from the enclosed delivery channel while driving a separating part of the claw arm to be arranged within the enclosed delivery channel. Here, the blocking part and separating part may be set front and back in the channel along a direction of transmitting the dyeing tank by the transmission mechanism.

In some embodiments, first dyeing solution may be injected into the dyeing tank in the beginning of a dyeing process, and then the smear that needs to be dyed may be put into the dyeing tank so as to avoid risk of hemolysis and ensure quality of dyeing.

When combining the above-described structures and operation processes of the smear machine, the above-described dyeing method of using a smear machine will be understood easily, so it needs no detailed description here.

The above detailed and specific description merely expresses several embodiments of this disclosure, and it should not be deemed to limit the scope of this disclosure. It should be noted that, for those of ordinary skill in the art, without departing from the inventive concept of this disclosure, a number of variations and modifications may be made, and such variations or modifications should be deemed to be included within the scope of this disclosure. Accordingly, the scope of protection of this disclosure should be defined by the appended claims.

The invention claimed is:

1. A dyeing device of a smear machine, comprising:
    a dyeing tank;
    a transmission mechanism for transmitting the dyeing tank circularly in an enclosed delivery channel; and
    a work position arranged in the enclosed delivery channel, wherein the work position comprises:
    a blocking and separating mechanism that blocks a dyeing tank to be treated in a current work position and separates a treated dyeing tank so as to transmit a separated dyeing tank to a next work position along the enclosed delivery channel by the transmission mechanism;
    a reagent supplying and discharging mechanism that injects and/or discharges a reagent to/from the dyeing tank; and
    a driving mechanism for driving the blocking and separating mechanism;
    wherein the dyeing tank comprises a body; the body is equipped with an opening cavity for accommodating a reagent and a smear; and both sides of the body are equipped with a suspension end for suspending the dyeing tank on the transmission mechanism; wherein the suspension end is equipped with a slot for separation by the blocking and separating mechanism.

2. The dyeing device of claim 1, wherein the transmission mechanism comprises a round tray driven by a motor, and the round tray is supplied with an annular opening for suspending the dyeing tank.

3. The dyeing device of claim 1, wherein the blocking and separating mechanism comprises a claw arm that is linked with the driving mechanism; the claw arm is driven to move by the driving mechanism; and the claw arm comprises a blocking part, a separating part, and a linking part for fixedly connecting the blocking part and the separating part; wherein the blocking part and the separating part are driven by the driving mechanism to be alternately located in the enclosed delivery channel of the dyeing tank, and the blocking part and the separating part are set front and back in the channel along a direction of transmitting the dyeing tank by the transmission mechanism.

4. The dyeing device of a smear machine of claim 3, wherein the dyeing device of a smear machine can comprise two claw arms, and the blocking part and the separating part of each claw arm are set on both sides of a target dyeing tank; wherein the blocking parts of the two claw arms are both set in a front orientation along a direction of transmitting the target dyeing tank, and the separating parts of the two claw arms are both set in a rear orientation along the direction of transmitting the target dyeing tank.

5. The dyeing device of claim 1, wherein each work position also comprises a detection device that detects a position of the dyeing tank and connects with the driving mechanism; and the dyeing tank also comprises a position detection plate for detection.

* * * * *